United States Patent [19]

Munson, Jr. et al.

[11] 4,343,804

[45] Aug. 10, 1982

[54] 4-AMINO-3-QUINOLINECARBOXYLIC ACIDS AND ESTERS-ANTISECRETORY ANTI-ULCER COMPOUNDS

[75] Inventors: Harry R. Munson, Jr.; Reevis S. Alphin, both of Richmond, Va.

[73] Assignee: A. H. Robins Company, Inc., Richmond, Va.

[21] Appl. No.: 127,153

[22] Filed: Mar. 4, 1980

Related U.S. Application Data

[63] Continuation-in-part of Ser. No. 23,981, Mar. 26, 1979, abandoned.

[51] Int. Cl.$^3$ .............................................. A61K 31/47
[52] U.S. Cl. .................................... 424/258; 546/159; 546/160; 546/161; 546/162
[58] Field of Search ................ 424/258; 546/159, 160, 546/161, 162

[56] References Cited

U.S. PATENT DOCUMENTS

3,470,186  9/1969  Hanifin et al. ...................... 260/287

OTHER PUBLICATIONS

Hanifin et al., *J. Med. Chem.*, 1969, 12(6) 1096–7.
Sen et al., *Chem. Abstr.*, vol. 52, 13732, (1958).
*J. Med. Pharm. Chem.*, 5 546–58 (1962).
Kermack et al., *J. Chem. Soc.*, 1951, 1389–92.

*Primary Examiner*—Frederick E. Waddell

[57] ABSTRACT

A method of reducing gastric acidity and treating peptic ulcers and pharmaceutical compositions therefor with certain 4-amino-3-quinolinecarboxylic acids and esters are disclosed. Illustrative of compounds useful in the method which relies on activity as antisecretory activity is the novel compound ethyl 8-methoxy-4-[(2-methylphenyl)amino]-3-quinolinecarboxylate which has the formula:

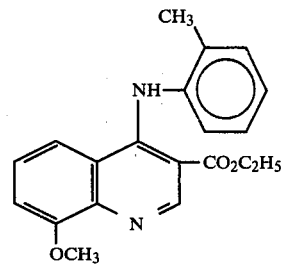

104 Claims, No Drawings

4-AMINO-3-QUINOLINECARBOXYLIC ACIDS AND ESTERS-ANTISECRETORY ANTI-ULCER COMPOUNDS

This application is a continuation-in-part of our copending application Ser. No. 023,981, filed Mar. 26, 1979, now abandoned.

BACKGROUND OF THE INVENTION

1. Field of Invention

The present invention relates to certain 4-amino-3-quinolinecarboxylic acids and esters and novel pharmaceutical use and compositions therefor. More particularly, the invention relates to certain 4-amino-3-quinolinecarboxylic acids and esters which reduce gastric secretion stimulated by secretagogues such as histamine, tetragastrin, and food and as such are useful in preventing or treating peptic ulcers in mammals. Certain of the compounds are novel.

2. Description of the Prior Art

Diuretic and antidepressant activity in certain 4-anilino-3-quinolinecarboxylic acid esters and 6-chloro derivatives thereof have been disclosed by Hanifin, J. W. in U.S. Patent No. 3,470,186 and *J. Med. Chem.* 1969, 12(6), 1096-7.

Kermack et al., *J. Chem. Soc.*, 1951, 1389-92 appears to disclose the preparation of 6-substituted 4-anilino-3-quinolinecarboxylic acids and esters therefrom. Sen et al., *J. Indian Chem. Soc.*, 34, 906-8 (1957) appears to disclose the preparation of 7-substituted 4-amino-3-quinolinecarboxylic amides. Elslager et al., *J. Med. Pharm. Chem.* 5, 546-58 (1962) discloses the preparation of 4-anilino-7-chloro-3-quinolinecarboxylic acid and its ethyl ester.

Antisecretory or anti-ulcer activities for 4-amino-3-quinolinecarboxylic acids and esters have not been disclosed prior to this invention.

SUMMARY OF THE INVENTION

The compounds useful in the novel method of inhibiting secretion of hydrochloric acid and treating peptic ulcers in mammals, in the present invention, are 4-amino-3-quinolinecarboxylic acids and esters which have the formula:

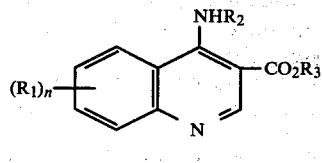

wherein:
$R_1$ is selected from the group consisting of loweralkyl, phenyl, O-loweralkyl, S-loweralkyl, halogen, trifluoromethyl, cyano and dialkylamino,
$R_2$ is selected from the group consisting of loweralkyl, phenyl, phenylloweralkyl or phenyl substituted by 1–3 radicals taken from among loweralkyl, O-loweralkyl, S-loweralkyl, halogen, cyano, hydroxy, carbamoyl, carboxy, acetyl, trifluoromethyl, and nitro,
$R_3$ is selected from the group consisting of hydrogen, loweralkyl, loweralkyldimethylamino, loweralkyl-loweralkoxy, and allyl,
n is 0, 1 or 2, and
the pharmaceutically acceptable addition salts thereof.

The antisecretory effect of reduced flow of gastric juice and hydrochloric acid in pyloric-ligated rats was demonstrated when the esters of 4-amino-3-quinolinecarboxylic acids of this invention were administered orally, subcutaneously, intraperitoneally, intraduodenally and intravenously. Effective ulceration reduction was also demonstrated in pyloric-ligated rats. The compounds of Formula I as stated hereinabove also were shown to reduce gastric secretion induced, for example, by histamine, tetragastrin and methacholine. Gastric acid output in Heidenhain pouch dogs stimulated with food was also reduced.

Accordingly, it is an object of the present invention to provide a novel method of controlling excess gastric acid output in mammals which comprises administering an acid-reducing amount of a compound of Formula I wherein $R_1$, $R_2$, $R_3$ and n are as hereinabove defined.

Another object is to provide a novel method of treating mammals for peptic ulceration which comprises administering to the mammal an effective amount which is a peptic ulcer inhibiting amount of a 4-amino-3-quinolinecarboxylic acid or ester compound of Formula I wherein $R_1$, $R_2$, $R_3$, and n are as defined hereinabove.

Another object is to provide novel 4-amino-3-quinolinecarboxylic acids and esters particularly effective for their control of gastric ulcers.

Still another object is to provide pharmaceutical compositions for accomplishing the foregoing objects comprised of suitable pharmaceutical carriers, for various routes of administration, of certain of the compounds of this invention.

Additional objects and advantages of the present invention will be apparent to one skilled in the art and others will become apparent from the following description of the best mode of carrying out the present invention and from the appended claims.

The term "loweralkyl" as used in the specification and claims includes straight and branched chain radicals of up to eight carbon atoms inclusive and is exemplified by such groups as methyl, ethyl, propyl, isopropyl, butyl, isobutyl, tertiary butyl, amyl, isoamyl, hexyl, heptyl, octyl and the like.

Representative of "phenylloweralkyl" radicals are benzyl (phenylmethyl), α-methylbenzyl, phenylethyl, phenylpropyl, phenylbutyl, and the like.

The compounds of the present invention are prepared from appropriate 4-chloro-3-quinolinecarboxylic acid esters as represented by the following equation:

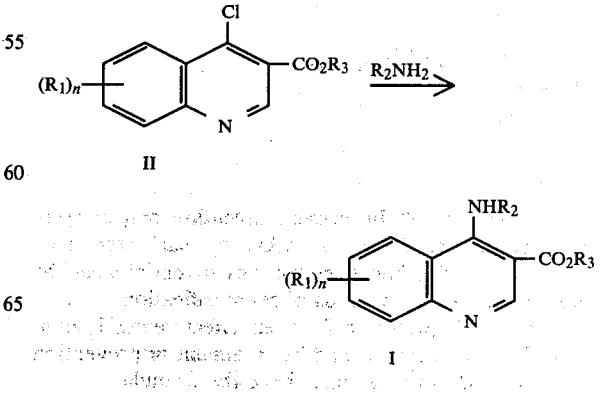

wherein R₁, R₂, and n are as hereinabove defined, and R₃ is loweralkyl.

The Formula II compounds were prepared by chlorinating appropriate 4-hydroxy-3-quinolinecarboxylic acid esters with phosphorous oxychloride generally by the method described by Kermack & Storey, J. Chem. Soc. 1951, pp 1389-92. The equation is:

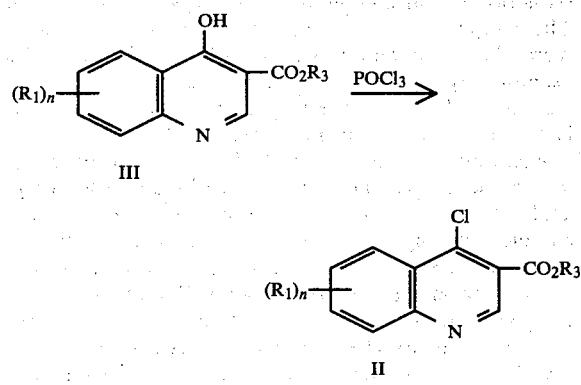

wherein R₁ and n are as defined hereinabove, and R₃ is loweralkyl.

The Formula III compounds wherein R₃ is ethyl were prepared by heating a mixture of appropriately substituted anilines and diethyl ethoxymethylenemalonate to form an intermediate anilinoacrylate and thereafter cyclizing in a high boiling solvent such as diphenyloxide as described by Price and Roberts in J. Amer. Chem. Soc. 68, 1204-8. The reaction is represented by the following equation:

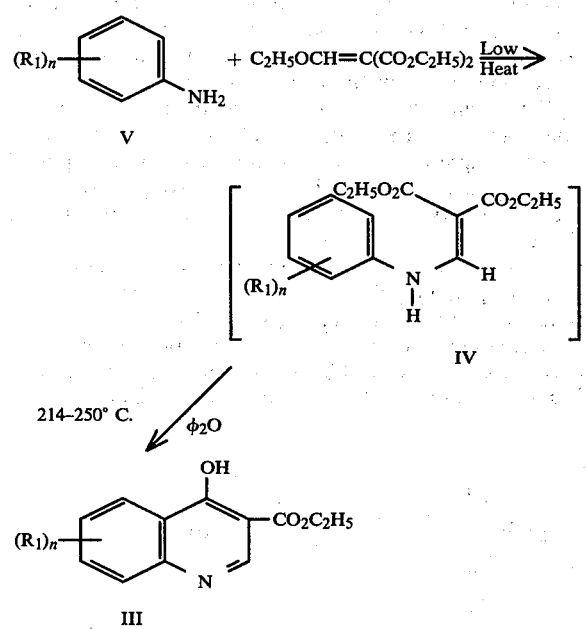

Acids (R₃=H) of the present invention may be prepared from esters (R₃=loweralkyl) by usual methods of hydrolysis and other esters of this invention may be prepared by usual methods of re-esterification.

Compounds preferred for their effectiveness in control of gastric secretion and/or treatment or prevention of peptic ulcers in mammals have the formula:

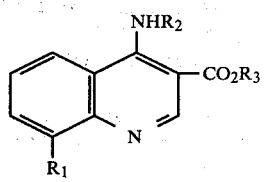

wherein:
R₁ is selected from the group consisting of loweralkyl, phenyl, O-loweralkyl, S-loweralkyl, halogen, trifluoromethyl, cyano and dialkylamino,
R₂ is selected from the group consisting of loweralkyl, phenyl, phenylloweralkyl or phenyl substituted by 1-3 radicals taken from among loweralkyl, O-loweralkyl, S-loweralkyl, halogen, cyano, carbamoyl, carboxy, acetyl, trifluoromethyl, and nitro,
R₃ is selected from the group consisting of hydrogen, loweralkyl, loweralkyldimethylamino, loweralkyl-loweralkoxy, and allyl, and
the pharmaceutically acceptable addition salts thereof.

For example, the effect of ethyl 8-methoxy-4-[(2-methylphenyl)amino]-3-quinolinecarboxylate hydrochloride on histamine-induced gastric secretion was found to be over 43% more effective than ethyl 6-methoxy-4-[(2-methylphenyl)amino]-3-quinolinecarboxylate at one half the dosage level.

Utilizing the foregoing method described by Price and Roberts, the following ethyl-4-hydroxy-3-quinolinecarboxylates of Formula II were prepared from diethylethoxymethoxymalonate and aniline or known aniline derivatives as follows:

Ethyl 4-hydroxyquinoline-3-carboxylate from aniline; m.p. 280°-283° C.
Ethyl 4-hydroxy-8-methoxy-3-quinolinecarboxylate from 2-methoxyaniline; m.p. 243°-246° C.
Ethyl 4-hydroxy-8-ethoxy-3-quinolinecarboxylate from 2-ethoxyaniline; m.p. 198°-200° C.
Ethyl 4-hydroxy-5,8-dimethoxy-3-quinolinecarboxylate from 2,5-dimethoxyaniline; m.p. 197°-199.5° C.
Ethyl 4-hydroxy-8-methoxy-5-methyl-3-quinolinecarboxylate from 2-methoxy-5-methylaniline; m.p. 180°-182° C.
Ethyl 4-hydroxy-8-phenyl-3-quinolinecarboxylate from 2-aminobiphenyl; m.p. 250°-252.5° C.
Ethyl 4-hydroxy-8-methyl-3-quinolinecarboxylate from 2-methylaniline; m.p. 271°-274° C.
Ethyl 4-hydroxy-8-trifluoromethyl-3-quinolinecarboxylate from 2-trifluoromethylaniline; m.p. 211°-213.5° C.
Ethyl 4-hydroxy-8-methylthio-3-quinolinecarboxylate from 2-methylthioaniline; m.p. 201°-204° C.
Ethyl 4-hydroxy-8-chloro-3-quinolinecarboxylate from 2-chloroaniline; m.p. 255°-259° C.
Ethyl 4-hydroxy-6,8-dimethyl-3-quinolinecarboxylate from 2,4-dimethylaniline;
Ethyl 4-hydroxy-6-methoxy-3-quinolinecarboxylate from 4-methoxyaniline; m.p. 283°-287° C.
Ethyl 4-hydroxy-8-cyano-3-quinolinecarboxylate from 2-cyanoaniline; m.p. 234°-236° C.
Ethyl 4-hydroxy-7-methoxy-3-quinolinecarboxylate from 3-methoxyaniline; m.p. 280°-282.5° C.
Ethyl 4-hydroxy-8-dimethylamino-3-quinolinecarboxylate from 2-dimethylaminoaniline; m.p. 176°-180° C.

Preparation 1 illustrates the synthesis procedure used to make the 4-chloro compounds of Formula II which are the starting materials used in making compounds of Formula I.

PREPARATION 1

Ethyl 4-chloro-8-methoxy-3-quinolinecarboxylate

A stirred mixture of ethyl 4-hydroxy-8-methoxyquinoline-3-carboxylate, 66.63 g (0.269 mole) and phosphorous oxychloride (350 ml) was warmed until all the solid had dissolved and then heated at reflux temperature for two hours. After cooling to below 100° C. the mixture was concentrated in a rotary evaporator. The residual oil was dissolved in 100 ml acetone and the solution poured onto an ice-water mixture (800 ml). The mixture was neutralized with 6 N sodium hydroxide solution and the solid product extracted successively with 450 ml, 250 ml and 100 ml portions of methylene chloride. The extracts were combined, washed with water, dried over anhydrous magnesium sulfate and concentrated to yield 68.16 g crude product. This crude product was dissolved in 500 ml hot toluene and filtered to remove a small quantity of insoluble material. The toluene solution was filtered through a bed of 250 g fluorisil followed by two liters of toluene and four liters of chloroform. The purified solution was concentrated to give 64.17 g of oil (89%) which crystallized to an off-white solid on cooling. The solid melted at 75°–77° C.

Analysis: Calculated for $C_{13}H_{12}NO_3Cl$: C, 58.77; H, 4.55; N, 5.27. Found: C, 58.58; H, 4.61; N, 5.33.

PREPARATION 2–15

Utilizing the procedure of Preparation 1, and substuting appropriate ethyl 4-hydroxy-3-quinolinecarboxylates listed above III, the following ethyl 4-chloroquinoline-3-carboxylates were prepared and used directly.

(2) Ethyl 4-chloro-3-quinolinecarboxylate
(3) Ethyl 4-chloro-8-ethoxy-3-quinolinecarboxylate
(4) Ethyl 4-chloro-5,8-dimethoxy-3-quinolinecarboxylate
(5) Ethyl 4-chloro-8-methoxy-5-methyl-3-quinolinecarboxylate
(6) Ethyl 4-chloro-8-phenyl-3-quinolinecarboxylate
(7) Ethyl 4-chloro-8-methyl-3-quinolinecarboxylate
(8) Ethyl 4-chloro-8-trifluoromethyl-3-quinolinecarboxylate
(9) Ethyl 4-chloro-8-methylthio-3-quinolinecarboxylate
(10) Ethyl 4,8-dichloro-3-quinolinecarboxylate
(11) Ethyl 4-chloro-6,8-dimethyl-3-quinolinecarboxylate
(12) Ethyl 4-chloro-6-methoxy-3-quinolinecarboxylate
(13) Ethyl 4-chloro-8-cyano-3-quinolinecarboxylate
(14) Ethyl 4-chloro-7-methoxy-3-quinolinecarboxylate
(15) Ethyl 4-chloro-8-(dimethylamino)-3-quinolinecarboxylate.

A general procedure for preparing esters of Formula I ($R_3$=loweralkyl) of the present invention is to react an appropriate 4-chloro-3-quinolinecarboxylic acid ester with an appropriate amine in a polar aprotic solvent such as tetrahydrofuran or dioxane, following the reaction by thinlayer chromatography and modifying temperature and time to complete the reaction. In some instances the reacting amine may be used as the reaction solvent. Various solvents are used for recrystallizing. To prepare the free base from a salt the salt is dissolved and a base such as sodium hydroxide is added and the free base is extracted into a suitable organic solvent. To prepare additional salts the free base is mixed with an alcoholic solution of an acid, for example, phosphoric acid or sulfuric acid.

The foregoing is a general description of how to prepare the esters of the invention. The following Examples 1 and 2 generally illustrate the preparation of the ester compounds. The esters of Examples 3 to 71 and 74 to 80 were also prepared by reacting the appropriate amine with the appropriate ethyl 4-chloro-3-quinolinecarboxylate selected from Preparations 1 to 15. Examples 81–84 and 89 illustrate the preparation of esters wherein $R_3$ is loweralkyl, loweralkyldimethylamino, loweralkyl-loweralkoxy or allyl by the re-esterification of esters wherein $R_3$ is loweralkyl. Preparation of the acids and acid salts thereof of Formula I ($R_3$=H) is illustrated in Examples 72 and 73, wherein the ester is hydrolyzed to the acid. Metal salts of the acids such as alkali metal salts may also be prepared by usual methods of reacting with an alkali metal base and isolating the salts. Examples 85–88 further illustrate the conversion of free bases of esters of this invention to their acid addition salts. Physical data and analysis obtained are in Tables 1 and 2. The presentation of examples, however, shall not be construed as a limitation of the scope of the compounds of the invention set forth in Formula I.

EXAMPLE 1

Ethyl 8-Methoxy-4-[(2-methylphenyl)amino]-3-quinolinecarboxylate Hydrochloride

To a solution of 5.31 g (19.98 mmoles) of ethyl 4-chloro-8-methoxy-3-quinolinecarboxylate dissolved in 40 ml of tetrahydrofuran was added 2.15 g (20.06 mmoles) of o-toluidine dissolved in 40 ml of tetrahydrofuran. The solution was stirred with exclusion of moisture at 60° C. for 18 hours. The yellow solid precipitate was filtered and washed with isopropyl ether; yield 7.13 g (95.7%). The product was recrystallized three times from methylene chloride: ethyl acetate, m.p. 191°–193.5° C.

Analysis: Calculated for $C_{20}H_{21}ClN_2O_3$: C,64.43; H,5.68; N,7.51. Found: C,64.36; H,5.65; N,7.62.

EXAMPLE 2

Ethyl 4-(Phenylamino)-8-methoxy-3-quinolinecarboxylate

To a solution of 6.0 g (22.5 mmoles) of ethyl 4-chloro-8-methoxy-3-quinolinecarboxylate in 80 ml of tetrahydrofuran was added 2.3 g (24.8 mmoles) of aniline in 60 ml of tetrahydrofuran. The solution was briefly warmed and after standing for 10 minutes, a yellow solid began to precipitate. The mixture was kept at room temperature for 18 hours. The solvent was rotary evaporated. The residue dissolved in 200 ml of methanol and the pH made slightly basic (pH 8) with sodium bicarbonate. Water (700 ml) was added and an oil formed which solidified and after standing, additional solid crystallized. The solid was filtered and air-dried to give 6.9 g (95%) of crude material. The solid was dissolved in 300 ml of hot isooctane and the solution was charcoaled and filtered. The volume of the filtrate was reduced to 150 ml. Upon cooling, pale yellow needles separated; 6.5 g (89%); m.p. 120°–121° C.

Analysis: Calculated for $C_{19}H_{18}N_2O_3$: C,70.79; H,5.63; N,8.69. Found: C,70.91; H,5.65; N,8.77.

EXAMPLES 3 TO 71

3. Ethyl 8-methoxy-4-[(2-methylphenyl)amino]-3-quinolinecarboxylate by neutralization of Example 1.
4. Ethyl 8-methoxy-4-[(2-methylphenyl)amino]-3-quinolinecarboxylate sulfate (1:1) from Example 3 and sulfuric acid.
5. Ethyl 8-methoxy-4-[(2-methylphenyl)amino]-3-quinolinecarboxylate phosphate (1:1) from Example 3 and phosphoric acid.
6. Ethyl 8-methoxy-4-(phenylamino)-3-quinolinecarboxylate hydrochloride from Preparation 1 and aniline.
7. Ethyl 8-methoxy-4-[(2-methoxyphenyl)amino]-3-quinolinecarboxylate hydrochloride from Preparation 1 and o-anisidine.
8. Ethyl 8-methoxy-4-[(2-methylthiophenyl)amino]-3-quinolinecarboxylate hydrochloride from Preparation 1 and 2-methylthioaniline.
9. Ethyl 4-[(2-chlorophenyl)amino]-8-methoxy-3-quinolinecarboxylate hydrochloride from Preparation 1 and 2-chloroaniline.
10. Ethyl 4-[(2-cyanophenyl)amino]-8-methoxy-3-quinolinecarboxylate hydrochloride from Preparation 1 and 2-aminobenzonitrile.
11. Ethyl 4-[(2-trifluoromethylphenyl)amino]-8-methoxy-3-quinolinecarboxylate hydrochloride from Preparation 1 and 2-trifluoromethylaniline.
12. Ethyl 4-{[2-(aminocarbonyl)phenyl]amino}-8-methoxy-3-quinolinecarboxylate monohydrochloride ethanol (5:2) from Preparation 1 and anthranilamide.
13. Ethyl 4-[(2-fluorophenyl)amino]-8-methoxy-3-quinolinecarboxylate hydrochloride from Preparation 1 and 2-fluoroaniline.
14. Ethyl 4-[(2-acetylphenyl)amino]-8-methoxy-3-quinolinecarboxylate hydrochloride from Preparation 1 and 2'-aminoacetophenone.
15. Ethyl 4-(butylamino)-8-methoxy-3-quinolinecarboxylate hydrochloride from Preparation 1 and n-butylamine.
16. Ethyl 8-methoxy-4-[(3-methylphenyl)amino]-3-quinolinecarboxylate hydrochloride monohydrate from Preparation 1 and m-toluidine.
17. Ethyl 8-methoxy-4-[(4-methylphenyl)amino]-3-quinolinecarboxylate hydrochloride monohydrate from Preparation 1 and p-toluidine.
18. Ethyl 8-methoxy-4-{[(2-methoxyphenyl)methyl]amino}-3-quinolinecarboxylate from Preparation 1 and 2-methoxybenzylamine.
19. Ethyl 8-methoxy-4-[(2-6-dimethylphenyl)amino]-3-quinolinecarboxylate from Preparation 1 and 2,6-dimethylaniline.
20. Ethyl 8-methoxy-4-[(2,6-dimethylphenyl)amino]-3-quinolinecarboxylate hydrobromide from Example 18 and HBr.
21. Ethyl 8-methoxy-4-[(1-phenylethyl)amino]-3-quinolinecarboxylate monohydrate from Preparation 1 and α-methylbenzylamine.
22. Ethyl 4-[(2-chloro-5-methoxyphenyl)amino]-8-methoxy-3-quinolinecarboxylate hydrobromide from Preparation 1 and 2-chloro-5-methoxyaniline.
23. Ethyl 8-methoxy-4-[(3-methylthio)phenyl]amino-3-quinolinecarboxylate from Preparation 1 and 3-methylmercaptoaniline.
24. Ethyl 4-benzylamino-8-methoxy-3-quinolinecarboxylate phosphate (1:1) methanolate (1:1) from Preparation 1 and benzylamine.
25. Ethyl 8-methoxy-4-[(2,4-dimethoxyphenyl)amino]-3-quinolinecarboxylate from Preparation 1 and 2,4-dimethoxyaniline.
26. Ethyl 4-[(2-ethoxyphenyl)amino]-8-methoxy-3-quinolinecarboxylate hydrochloride from Preparation 1 and 2-ethoxyaniline.
27. Ethyl 8-methoxy-4-[4-methoxy-2-methylphenyl)amino]-3-quinolinecarboxylate from Preparation 1 and 2-methyl-4-methoxyaniline.
28. Ethyl 4-[(2-ethylphenyl)amino]-8-methoxy-3-quinolinecarboxylate from Preparation 1 and 2-ethylaniline.
29. Ethyl 4-[(2-ethylphenyl)amino]-8-methoxy-3-quinolinecarboxylate phosphate (1:2) from Example 28 and anhyd. $H_3PO_4$.
30. Ethyl 4-[(2-ethylphenyl)amino]-8-methoxy-3-quinolinecarboxylate sulfate (1:1) from Example 28 and alcoholic $H_2SO_4$.
31. Ethyl 4-[(2,6-dichlorophenyl)amino]-8-methoxy-3-quinolinecarboxylate from Preparation 1 and 2,6-dichloroaniline.
32. Ethyl 8-methoxy-4-[(2-methyl-5-nitrophenyl)amino]-3-quinolinecarboxylate from Preparation 1 and 2-methyl-5-nitroaniline.
33. Ethyl 8-methoxy-4-{[(2-methylphenyl)methyl]amino}-3-quinolinecarboxylate hydrochloride ethanol (2:1) from Preparation 1 and o-methylbenzylamine, ethanol and hydrochloride.
34. Ethyl 8-ethoxy-4-[(2-methylphenyl)amino]-3-quinolinecarboxylate hydrochloride from Preparation 3 and o-toluidine.
35. Ethyl 8-ethoxy-4-[2-(trifluoromethylphenyl)amino]-3-quinolinecarboxylate hydrobromide from Preparation 3 and o-trifluoromethylaniline.
36. Ethyl 8-ethoxy-4-[(2-methoxyphenyl)amino]-3-quinolinecarboxylate hydrochloride from Preparation 3 and o-anisidine.
37. Ethyl 8-ethoxy-4-[2-(methylthiophenyl)amino]-3-quinolinecarboxylate phosphate (1:1) from Preparation 3 and methylthioaniline and alcoholic $H_3PO_4$.
38. Ethyl 5,8-dimethoxy-4-(phenylamino)-3-quinolinecarboxylate hydrochloride hemihydrate from Preparation 4 and aniline.
39. Ethyl 5,8-dimethoxy-4-[(2-methylphenyl)amino]-3-quinolinecarboxylate from Preparation 4 and o-toluidine.
40. Ethyl 7-methoxy-4-[(2-methylphenyl)amino]-3-quinolinecarboxylate hydrochloride from Preparation 14 and o-toluidine.
41. Ethyl 4-(phenylamino)-6-methoxy-3-quinolinecarboxylate from Preparation 12 and aniline.
42. Ethyl 6-methoxy-4-[(2-methylphenyl)amino]-3-quinolinecarboxylate from Preparation 12 and o-toluidine.
43. Ethyl 8-methoxy-4-[(2-methoxyphenyl)amino]-5-methyl-3-quinolinecarboxylate dihydrochloride from Preparation 5 and o-anisidine.
44. Ethyl 8-methoxy-5-methyl-4-[2-(methylthiophenyl)amino]-3-quinolinecarboxylate phosphate (2:3) from Preparation 5 and 2-methylthioaniline.

45. Ethyl 8-methoxy-5-methyl-4-[(2-methylphenyl)amino]-3-quinolinecarboxylate from Preparation 5 and o-toluidine.
46. Ethyl 4-[2-(methylphenyl)amino]-8-trifluoromethyl-3-quinolinecarboxylate from Preparation 8 and o-toluidine.
47. Ethyl 4-[(2-methylphenyl)amino]-8-methylthio-3-quinolinecarboxylate from Preparation 9 and o-toluidine.
48. Ethyl 4-[(2-methoxyphenyl)amino]-8-methylthio-3-quinolinecarboxylate hydrochloride from Preparation 9 and o-toluidine.
49. Ethyl 8-methylthio-4-[(2-methylthiophenyl)amino]-3-quinolinecarboxylate from Preparation 9 and 2-methylthioaniline.
50. Ethyl 8-methyl-4-[2-(methylthiophenyl)amino]-3-quinolinecarboxylate hydrochloride from Preparation 7 and 2-methylthioaniline.
51. Ethyl 4-[(2-methoxyphenyl)amino]-8-methyl-3-quinolinecarboxylate hydrochloride from Preparation 7 and o-anisidine.
52. Ethyl 8-methyl-4-[(2-methylphenyl)methyl]amino-3-quinolinecarboxylate hydrobromide from Preparation 7 and 2-methylbenzylamine.
53. Ethyl 8-chloro-4-[(2-methoxyphenyl)amino]-3-quinolinecarboxylate hydrochloride from Preparation 10 and o-anisidine.
54. Ethyl 8-cyano-4-[(2-methylphenyl)amino]-3-quinolinecarboxylate hydrochloride from Preparation 13 and aniline.
55. Ethyl 4-(phenylamino)-8-phenyl-3-quinolinecarboxylate from Preparation 6 and aniline.
56. Ethyl 4-[(2-carboxyphenyl)amino]-8-phenyl-3-quinolinecarboxylate hydrochloride hemihydrate from Preparation 6 and 2-aminobenzoic acid.
57. Ethyl 4-benzylamino-8-phenyl-3-quinolinecarboxylate from Preparation 6 and benzylamine.
58. Ethyl 4-(phenylamino)-6,8-dimethyl-3-quinolinecarboxylate from Preparation 11 and aniline.
59. Ethyl 4-(phenylamino)-3-quinolinecarboxylate from Preparation 2 and aniline.
60. Ethyl 4-(phenylamino)-3-quinolinecarboxylate hydrochloride from Preparation 2 and aniline.
61. Ethyl 4-benzylamino-3-quinolinecarboxylate hydrochloride from Preparation 2 and benzylamine.
62. Ethyl 4-[(2-methylphenyl)amino]-3-quinolinecarboxylate hydrochloride from Preparation 2 and o-toluidine.
63. Ethyl 4-[2-(trifluoromethylphenyl)amino]-3-quinolinecarboxylate hydrochloride from Preparation 2 and 2-trifluoromethylaniline.
64. Ethyl 4-[(2-methoxyphenyl)amino]-3-quinolinecarboxylate hydrochloride from Preparation 2 and o-anisidine.
65. Ethyl 4-[(2-methylthiophenyl)amino]-3-quinolinecarboxylate hydrochloride from Preparation 2 and 2-methylthioaniline.
66. Ethyl 4-[(4-methoxy-2-methylphenyl)amino]-3-quinolinecarboxylate hydrochloride from Preparation 2 and 2-methyl-4-methoxyaniline.
67. Ethyl 4-[(2-chlorophenyl)amino]-3-quinolinecarboxylate hydrochloride from Preparation 2 and 2-chloroaniline.
68. Ethyl 8-(dimethylamino)-4-(phenylamino)-3-quinolinecarboxylate hydrochloride from Preparation 15 and aniline.
69. Ethyl 8-(dimethylamino)-4-[(2-methylphenyl)amino]-3-quinolinecarboxylate from Preparation 15 and o-toluidene.
70. Ethyl 8-cyano-4-(phenylamino)-3-quinolinecarboxylate from Preparation 13 and aniline.
71. Ethyl [(2-hydroxyphenyl)amino]-8-methoxy-3-quinolinecarboxylate from Preparation 1 and o-hydroxyaniline.

EXAMPLE 72

8-Methoxy-4-[(2-methylphenyl)amino]-3-quinolinecarboxylic Acid

A mixture of Ethyl 8-methoxy-4-[(2-methylphenyl)amino]-3-quinolinecarboxylate, 15.00 g (0.0445 mole), 100 ml of 3 N sodium hydroxide solution and 100 ml of ethanol was stirred at room temperature for 16 hours. The mixture was diluted with 300 ml of water and acidified to pH 6.8 with 6 N hydrochloric acid solution. The precipitate was collected by filtration, washed in succession with water and acetone and air dried for about 1.5 hr. Weight of solid was 13.41 g (98%), m.p. 272° C. (d).

Analysis: Calculated for $C_{18}H_{16}N_2O_3$: C,70.12; H,5.23; N,9.09. Found: C,70.10; H,5.27; N,9.09.

EXAMPLE 73

8-Methoxy-4-[(2-methylphenyl)amino]-3-quinolinecarboxylic Acid Hydrochloride

A portion of the 8-methoxy-4-[(2-methylphenyl)amino]-3-quinolinecarboxylic acid, 4.35 g from Example 72 was triturated with 100 ml hot absolute ethanol. After cooling, the solid was collected by filtration and air dried to give 3.87 g. The solid was suspended in 25 ml of absolute ethanol and excess ethereal hydrogen chloride solution added. A clear solution was obtained. Addition of isopropyl ether produced a yellow precipitate which was collected and recrystallized from absolute ethanol-isopropyl ether to yield 3.14 g solid m.p. 257° C. (d).

Analysis: Calculated for $C_{18}H_{17}N_2O_3Cl$: C,62.70; H,4.97; N,8.12. Found: C,62.53; H,4.93; N,8.18.

EXAMPLES 74–80

74. Ethyl 8-methyl-4-[(2-methylphenyl)amino]-3-quinolinecarboxylate monohydrochloride from Preparation 7 and o-toluidine.
75. Ethyl 8-methoxy-4-[[2-(1-methylethyl)phenyl]amino]-3-quinolinecarboxylate from Preparation 1 and o-isopropylaniline.
76. Ethyl 8-chloro-4-[(2-methylphenyl)amino]-3-quinolinecarboxylate from Preparation 10 and o-toluidine.
77. Ethyl [(2-chloro-6-methylphenyl)amino]-8-methoxy-3-quinolinecarboxylate monohydrochloride from Preparation 1 and 2-chloro-6-methylaniline.
78. Ethyl 8-methoxy-4-[(2,3-dimethylphenyl)amino]-3-quinolinecarboxylate monosulfate from Preparation 1 and 2,3-dimethylaniline.
79. Ethyl 8-methoxy-4-[(2-nitrophenyl)amino]-3-quinolinecarboxylate from Preparation 1 and 2-nitroaniline.
80. Ethyl 8-methoxy-4-[(2-nitrophenyl)amino]-3-quinolinecarboxylate, ethylsulfate (1:1), ethanol (1:1) from Example 79 and concentrated sulfuric acid in absolute ethanol.

EXAMPLE 81

1-Methylethyl 8-Methoxy-4-[(2-methylphenyl)amino]-3-quinolinecarboxylate, Monohydrochloride, Monohydrate To 150 ml of dry 2-propanol was added 2 sodium pellets followed by 5.38 g (15.99 mmoles) of ethyl 8-methoxy-4-[(2-methylphenyl)amino]-3-quinolinecarboxylate dissolved in 50 ml of dry 2-propanol. The solution was stirred and refluxed with exclusion of moisture for 6 hrs. during which time 120 ml of distillate was collected in a Dean-Starke trap and discarded. The solvent was evaporated and the residue was dissolved in 50 ml of 2.9 M hydrochloric acid and 100 ml of water added thereto. The solution was adjusted to a pH of 8 with 1 M aqueous sodium bicarbonate and the oil which separated was extracted three times with 100 ml of methylene chloride. The combined extracts were dried over magnesium sulfate. The solvent was evaporated to give 4.60 g (82%) of the free base of the titled compound having a m.p. of 120°–122° C. after recrystallization from acetone-hexane.

The free base was dissolved in isopropyl ether and ethereal hydrogen chloride added thereto. The solvent was evaporated and the residue recrystallized from methylene chloride-acetone to obtain the titled compound as a yellow crystalline solid having a m.p. of 140°–143° C.

EXAMPLE 82

2-(Methoxyethyl)-8-methoxy-4-[(2-methylphenyl)amino]-3-quinolinecarboxylate

Following the procedure of Example 81, the compound of Example 3 was re-esterified with 2-methoxyethanol to give the titled compound.

EXAMPLE 83

3-(Dimethylamino)ethyl 8-Methoxy-4-[(2-methylphenyl)amino]-3-quinolinecarboxylate Following a procedure similar to that given in Example 81, the compound of Example 3 was re-esterified with 2-dimethylaminoethanol substituting sodium ethoxide catalyst and toluene solvent to give the titled compound.

EXAMPLE 84

3-(Dimethylamino)propyl 8-Methoxy-4-[(2-methylphenyl)amino]-3-quinolinecarboxylate Following a procedure similar to that given in Example 81, the compound of Example 3 was re-esterified with 3-dimethylamino-1-propanol substituting toluene sovlent to give the title compound.

EXAMPLE 85

2-(Dimethylamino)ethyl 8-Methoxy-4-[(2-methylphenyl)amino]-3-quinolinecarboxylate, Fumarate (1:1.5)

The titled compound was prepared from the compound of Example 83 and fumaric acid.

EXAMPLE 86

3-(Dimethylamino)propyl 8-Methoxy-4-[(2-methylphenyl)amino]-3-quinolinecarboxylate, Dihydrochloride, Monohydrate The titled compound was prepared from the compound of Example 84 and ethereal hydrogen chloride.

EXAMPLE 87

Ethyl 8-Methoxy-4-[(2-methylphenyl)amino]-3-quinolinecarboxylate, ethanesulfonate (1:1)(salt)

The titled compound was prepared from the compound of Example 3 and ethanesulfonic acid in absolute ethanol.

EXAMPLE 88

Ethyl 8-Methoxy-4-[(2-methylphenyl)amino]-3-quinolinecarboxylate, 2-Hydroxyethanesulfonate (1:1)(salt)

The titled compound was prepared from the compound of Example 3 and 2-hydroxyethylsulfonic acid in absolute ethanol.

EXAMPLE 89

Allyl 8-Methoxy-4-[(2-methylphenyl)amino]-3-quiolinecarboxylate

Following a procedure similar to Example 81, substituting allyl alcohol for 2-propanol, the titled compound is prepared.

TABLE 1

(Examples 1–88)

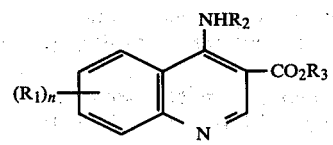

| Example | $R_1$ | $R_2$ | $R_3$ | Salt | M.P., °C. |
|---|---|---|---|---|---|
| 1 | 8-$CH_3O$— | 2-$CH_3$—$C_6H_4$— | $C_2H_5$— | HCl | 191–193.5 |
| 2 | 8-$CH_3O$— | $C_6H_5$— | $C_2H_5$— | — | 120–121 |
| 3 | 8-$CH_3O$— | 2-$CH_3$—$C_6H_4$— | $C_2H_5$— | — | 138.5–140 |
| 4 | 8-$CH_3O$— | 2-$CH_3$—$C_6H_4$— | $C_2H_5$— | $H_2SO_4$ | 192–194 |
| 5 | 8-$CH_3O$— | 2-$CH_3$—$C_6H_4$— | $C_2H_5$— | $H_3PO_4$ | 99–102 |
| 6 | 8-$CH_3O$— | $C_6H_5$— | $C_2H_5$— | HCl | 165.5–168 |
| 7 | 8-$CH_3O$— | 2-$CH_3O$—$C_6H_4$— | $C_2H_5$— | HCl | 204–207 |
| 8 | 8-$CH_3O$— | 2-$CH_3S$—$C_6H_4$— | $C_2H_5$— | HCl | 275–278 |

TABLE 1-continued
(Examples 1-88)

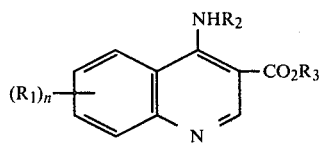

| Example | $R_1$ | $R_2$ | $R_3$ | Salt | M.P., °C. |
|---|---|---|---|---|---|
| 9 | 8-$CH_3O$— | 2-Cl—$C_6H_4$— | $C_2H_5$— | HCl | 193–194.5 |
| 10 | 8-$CH_3O$— | 2-CN—$C_6H_4$— | $C_2H_5$— | HCl | 204–206.5 |
| 11 | 8-$CH_3O$— | 2-$CF_3$—$C_6H_4$— | $C_2H_5$— | HCl | 199–201d |
| 12 | 8-$CH_3O$— | 2-$NH_2OC$—$C_6H_4$— | $C_2H_5$— | 1HCl. 0.4$C_2H_5OH$ | 251–154 |
| 13 | 8-$CH_3O$— | 2-F—$C_6H_4$— | $C_2H_5$— | HCl | 204–206 |
| 14 | 8-$CH_3O$— | 2-$CH_3CO$—$C_6H_4$— | $C_2H_5$— | HCl | 203–204d |
| 15 | 8-$CH_3O$— | $CH_3$(—$CH_2$)$_3$— | $C_2H_5$— | HCl | 171–172d |
| 16 | 8-$CH_3O$— | 3-$CH_3C_6H_4$ | $C_2H_5$— | HCl.$H_2O$ | 156–158d |
| 17 | 8-$CH_3O$— | 4-$CH_3C_6H_4$ | $C_2H_5$— | HCl.$H_2O$ | 155–156d |
| 18 | 8-$CH_3O$— | 2-$CH_3O$—$C_6H_4CH_2$— | $C_2H_5$— | — | 132–137 |
| 19 | 8-$CH_3O$— | 2,6($CH_3$)$_2C_6H_3$— | $C_2H_5$— | — | 160–163 |
| 20 | 8-$CH_3O$— | 2,6($CH_3$)$_2C_6H_3$— | $C_2H_5$— | HBr | 182–184 |
| 21 | 8-$CH_3O$— | $C_6H_5$($CH_3$)CH— | $C_2H_5$— | $H_2O$ | 97–99 |
| 22 | 8-$CH_3O$— | 2-Cl—5-$CH_3O$—$C_6H_3$— | $C_2H_5$— | HBr | 160–162 |
| 23 | 8-$CH_3O$— | 3-$CH_3S$—$C_6H_4$— | $C_2H_5$— | — | 123–124.5 |
| 24 | 8-$CH_3O$— | $C_6H_5CH_2$— | $C_2H_5$— | $H_3PO_4$. $CH_3OH$ | 221–223 |
| 25 | 8-$CH_3O$— | 2,4($CH_3O$)$_2$—$C_6H_3$— | $C_2H_5$— | — | 128–131 |
| 26 | 8-$CH_3O$— | 2-$C_2H_5O$—$C_6H_4$— | $C_2H_5$— | HCl | 208d |
| 27 | 8-$CH_3O$— | 2-$CH_3$—4-$CH_3O$—$C_6H_3$— | $C_2H_5$— | — | 175–176 |
| 28 | 8-$CH_3O$— | 2-$C_2H_5$—$C_6H_4$— | $C_2H_5$— | — | 152–153 |
| 29 | 8-$CH_3O$— | 2-$C_2H_5$—$C_6H_4$— | $C_2H_5$— | 2$H_3PO_4$ | 140–142 |
| 30 | 8-$CH_3O$— | 2-$C_2H_5$—$C_6H_4$— | $C_2H_5$— | $H_2SO_4$ | 177–178.5 |
| 31 | 8-$CH_3O$— | 2,6-Cl—$C_6H_3$— | $C_2H_5$— | — | 178–180 |
| 32 | 8-$CH_3O$— | 2-$CH_3$—5-$NO_2$—$C_6H_3$— | $C_2H_5$— | — | 251.5–253 |
| 33 | 8-$CH_3O$— | 2-$CH_3$—$C_6H_4CH_2$— | $C_2H_5$— | HCl. ½$C_2H_5OH$ | 197.5–198 |
| 34 | 8-$C_2H_5O$— | 2-$CH_3$—$C_6H_4$— | $C_2H_5$ | HCl | 208–209 |
| 35 | 8-$C_2H_5O$— | 2-$CF_3$—$C_6H_4$— | $C_2H_5$— | HBr | 185–191d |
| 36 | 8-$C_2H_5O$— | 2-$CH_3O$—$C_6H_4$— | $C_2H_5$— | HCl | 205–206.5 |
| 37 | 8-$C_2H_5O$— | 2-$CH_3S$—$C_6H_4$— | $C_2H_5$— | $H_3PO_4$ | 185–190 |
| 38 | 5,8($CH_3O$)$_2$— | $C_6H_5$— | $C_2H_5$— | HCl.½$H_2O$ | 166–167 |
| 39 | 5,8($CH_3O$)$_2$— | 2-$CH_3$—$C_6H_4$— | $C_2H_5$— | — | 156–158d |
| 40 | 7-$CH_3O$— | 2-$CH_3$—$C_6H_4$— | $C_2H_5$— | HCl | 147–159d |
| 41 | 6-$CH_3O$— | $C_6H_5$— | $C_2H_5$— | — | 99.5–102.5 |
| 42 | 6-$CH_3O$— | 2-$CH_3$—$C_6H_4$— | $C_2H_5$— | HCl | 193d |
| 43 | 5-$CH_3$—8-$CH_3O$— | 2-$CH_3O$—$C_6H_4$— | $C_2H_5$— | 2HCl | 183–185d |
| 44 | 5-$CH_3$—8-$CH_3O$— | 2-$CH_3S$—$C_6H_4$— | $C_2H_5$— | 1.5$H_3PO_4$ | 204–205 |
| 45 | 5-$CH_3$—8-$CH_3O$— | 2-$CH_3$—$C_6H_4$— | $C_2H_5$— | — | 167.5–169 |
| 46 | 8-$CF_3$— | 2-$CH_3$—$C_6H_4$— | $C_2H_5$— | — | 147–148 |
| 47 | 8-$CH_3S$— | 2-$CH_3$—$C_6H_4$— | $C_2H_5$— | — | 168–170 |
| 48 | 8-$CH_3S$— | 2-$CH_3O$—$C_6H_4$— | $C_2H_5$— | HCl | 169–172 |
| 49 | 8-$CH_3S$— | 2-$CH_3S$—$C_6H_4$— | $C_2H_5$— | — | 140.5–142 |
| 50 | 8-$CH_3$— | 2-$CH_3S$—$C_6H_4$— | $C_2H_5$— | HCl | 172–174d |
| 51 | 8-$CH_3$— | 2-$CH_3O$—$C_6H_4$— | $C_2H_5$— | HCl | 186–188 |
| 52 | 8-$CH_3$— | 2-$CH_3$—$C_6H_4CH_2$— | $C_2H_5$— | HBr | 182–183 |
| 53 | 8-Cl— | 2-$CH_3O$—$C_6H_4$— | $C_2H_5$— | HCl | 203–205d |
| 54 | 8-CN— | 2-$CH_3$—$C_6H_4$— | $C_2H_5$— | HCl | 215–219 |
| 55 | 8-$C_6H_5$— | $C_6H_5$— | $C_2H_5$— | — | 123–125 |
| 56 | 8-$C_6H_5$— | 2-COOH—$C_6H_4$— | $C_2H_5$— | HCl.½$H_2O$ | 213–214 |
| 57 | 8-$C_6H_5$— | $C_6H_5CH_2$— | $C_2H_5$— | — | 130–131 |
| 58 | 6,8($CH_3$)$_2$— | $C_6H_5$— | $C_2H_5$— | — | 164.5–165 |
| 59 | H— | $C_6H_5$— | $C_2H_5$— | — | 100–102[a] |
| 60 | H— | $C_6H_5$— | $C_2H_5$— | HCl | 193–195d |
| 61 | H— | $C_6H_5CH_2$— | $C_2H_5$— | HCl | 195.5–196 |
| 62 | H— | 2-$CH_3$—$C_6H_4$— | $C_2H_5$— | HCl | 170–171d |
| 63 | H— | 2-$CF_3$—$C_6H_4$— | $C_2H_5$— | HCl | 168.5–170 |
| 64 | H— | 2-$CH_3O$—$C_6H_4$— | $C_2H_5$— | HCl | 172–174.5 |
| 65 | H— | 2-$CH_3S$—$C_6H_4$— | $C_2H_5$— | HCl | 186–187d |
| 66 | H— | 2-$CH_3$—4-$OCH_3$—$C_6H_3$— | $C_2H_5$— | HCl | 178–179d |
| 67 | H— | 2-Cl—$C_6H_4$— | $C_2H_5$ | HCl | 204–205d |
| 68 | 8-($CH_3$)$_2$N— | $C_6H_5$— | $C_2H_5$— | HCl | 179–181 |
| 69 | 8-($CH_3$)$_2$N— | 2-$CH_3$—$C_6H_4$— | $C_2H_5$— | — | 110–114 |
| 70 | 8-CN | $C_6H_5$— | $C_2H_5$— | — | 194–196 |
| 71 | 8-$CH_3O$— | 2-OH—$C_6H_4$— | $C_2H_5$— | — | 229–231 |
| 72 | 8-$CH_3O$— | 2-$CH_3$—$C_6H_4$— | H | — | 272(d) |
| 73 | 8-$CH_3O$— | 2-$CH_3$—$C_6H_4$ | H | HCl | 257 |
| 74 | 8-$CH_3$— | 2-$CH_3$—$C_6H_4$— | $C_2H_5$— | HCl | 162–164 |

TABLE 1-continued
(Examples 1-88)

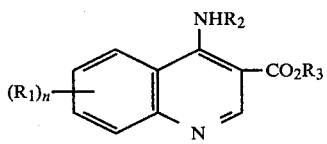

| Example | R₁ | R₂ | R₃ | Salt | M.P., °C. |
|---|---|---|---|---|---|
| 75 | 8-$CH_3O$— | 2-$(CH_3)_2CH$—$C_6H_4$— | $C_2H_5$— | — | 136–138 |
| 76 | 8-Cl | 2-$CH_3$—$C_6H_4$— | $C_2H_5$— | — | 189–191 |
| 77 | 8-$CH_3O$— | 2-$CH_3$—$C_6H_4$— | $C_2H_5$— | HCl | 207–209 |
| 78 | 8-$CH_3O$— | 2,3-$(CH_3)_2$—$C_6H_3$— | $C_2H_5$— | $H_2SO_4$ | 177–181 |
| 79 | 8-$CH_3O$— | 2-$NO_2$—$C_6H_4$— | $C_2H_5$— | — | 180–182 |
| 80 | 8-$CH_3O$— | 2-$NO_2$—$C_6H_4$— | $C_2H_5$— | $C_2H_5OH$ | 85–90 |
| 81 | 8-$CH_3O$— | 2-$CH_3$—$C_6H_4$— | $(CH_3)_2HC$— | $HCl.H_2O$ | 140–143 |
| 82 | 8-$CH_3O$— | 2-$CH_3$—$C_6H_4$— | $CH_3O(CH_2)_2$— | HCl | 184–187 |
| 83 | 8-$CH_3O$— | 2-$CH_3$—$C_6H_4$— | $(CH_3)_2N(CH_2)_2$— | — | 100–103 |
| 84 | 8-$CH_3O$— | 2-$CH_3$—$C_6H_4$— | $(CH_3)_2N(CH_2)_3$— | — | 95–97.5 |
| 85 | 8-$CH_3O$— | 2-$CH_3$—$C_6H_4$— | $(CH_3)_2N(CH_2)_2$— | fumarate | 186–189 |
| 86 | 8-$CH_3O$— | 2-$CH_3$—$C_6H_4$— | $(CH_3)_2N(CH_2)_3$— | $.H_2O$ .HCl | 177–180 |
| 87 | 8-$CH_3O$— | 2-$CH_3$—$C_6H_4$— | $C_2H_5$— | $CH_3CH_2$—$SO_2OH$ | 113–116 |
| 88 | 8-$CH_3O$ | 2-$CH_3$—$C_6H_4$— | $C_2H_5$ | $HO$—$CH_2CH_2SO_2OH$ | 142–145 |

(a)Compares with m.p. 99–100° C. given in J. Pharm. Chem. Soc. 1389 (1951).

TABLE 2
Analytical Data on Examples 1-88

| Ex. | Empirical Formula | Calculated C | Calculated H | Calculated N | Found C | Found H | Found N |
|---|---|---|---|---|---|---|---|
| 1 | $C_{20}H_{21}ClN_2O_3$ | 64.63 | 5.68 | 7.51 | 64.36 | 5.65 | 7.62 |
| 2 | $C_{19}H_{18}N_2O_3$ | 70.79 | 5.63 | 8.69 | 70.91 | 5.65 | 8.77 |
| 3 | $C_{20}H_{20}N_2O_3$ | 71.41 | 5.99 | 8.33 | 71.52 | 5.94 | 8.35 |
| 4 | $C_{20}H_{22}N_2O_7S$ | 55.29 | 5.10 | 6.45 | 55.68 | 5.02 | 6.42 |
| 5 | $C_{20}H_{23}N_2O_7P$ | 55.30 | 5.34 | 6.45 | 54.92 | 5.37 | 6.53 |
| 6 | $C_{19}H_{19}ClN_2O_3$ | 63.60 | 5.34 | 7.81 | 63.25 | 5.33 | 7.69 |
| 7 | $C_{20}H_{21}ClN_2O_4$ | 61.78 | 5.44 | 7.20 | 61.55 | 5.57 | 7.07 |
| 8 | $C_{20}H_{21}ClN_2O_3S$ | 59.33 | 5.23 | 6.92 | 59.04 | 5.38 | 6.87 |
| 9 | $C_{19}H_{18}Cl_2N_2O_3$ | 58.03 | 4.61 | 7.12 | 57.89 | 4.69 | 7.13 |
| 10 | $C_{20}H_{18}ClN_3O_3$ | 62.59 | 4.73 | 10.95 | 62.23 | 4.95 | 10.73 |
| 11 | $C_{20}H_{18}N_2O_3F_3Cl$ | 56.28 | 4.25 | 6.56 | 56.33 | 4.34 | 6.60 |
| 12 | $C_{104}H_{112}Cl_5N_{15}O_{22}$ | 59.44 | 5.37 | 10.00 | 59.25 | 5.21 | 10.03 |
| 13 | $C_{19}H_{18}N_2O_3FCl$ | 60.56 | 4.81 | 7.43 | 60.28 | 4.87 | 7.32 |
| 14 | $C_{21}H_{21}N_2O_4Cl$ | 62.92 | 5.28 | 6.99 | 62.56 | 5.48 | 6.76 |
| 15 | $C_{17}H_{23}N_2O_3Cl$ | 60.26 | 6.84 | 8.26 | 59.39 | 6.80 | 8.20 |
| 16 | $C_{20}H_{23}N_2O_4Cl$ | 61.46 | 5.93 | 7.17 | 61.40 | 5.92 | 7.21 |
| 17 | $C_{20}H_{23}N_2O_4Cl$ | 61.46 | 5.93 | 7.17 | 61.73 | 5.76 | 7.33 |
| 18 | $C_{21}H_{22}N_2O_4$ | 68.84 | 6.05 | 7.65 | 68.61 | 6.04 | 7.51 |
| 19 | $C_{21}H_{22}N_2O_3$ | 71.98 | 6.33 | 7.99 | 72.16 | 6.33 | 8.01 |
| 20 | $C_{21}H_{23}BrN_2O_3$ | 58.48 | 5.37 | 6.49 | 58.48 | 5.41 | 6.52 |
| 21 | $C_{21}H_{24}N_2O_4$ | 68.46 | 6.57 | 7.60 | 68.47 | 6.51 | 7.59 |
| 22 | $C_{20}H_{20}N_2O_4ClBr$ | 51.35 | 4.31 | 5.99 | 51.27 | 4.30 | 6.04 |
| 23 | $C_{20}H_{20}N_2O_3S$ | 65.20 | 5.47 | 7.60 | 65.18 | 5.48 | 7.66 |
| 24 | $C_{21}H_{27}N_2O_8P$ | 54.08 | 5.84 | 6.01 | 54.32 | 5.58 | 6.23 |
| 25 | $C_{21}H_{22}N_2O_5$ | 65.96 | 5.80 | 7.33 | 66.06 | 5.75 | 7.28 |
| 26 | $C_{21}H_{23}N_2O_4Cl$ | 62.61 | 5.75 | 6.95 | 62.61 | 5.84 | 6.94 |
| 27 | $C_{21}H_{22}N_2O_4$ | 68.84 | 6.05 | 7.65 | 68.94 | 6.06 | 7.68 |
| 28 | $C_{21}H_{22}N_2O_3$ | 71.98 | 6.33 | 7.99 | 72.02 | 6.29 | 8.03 |
| 29 | $C_{21}H_{28}N_2O_{11}P_2$ | 46.16 | 5.17 | 5.13 | 46.07 | 5.22 | 5.12 |
| 30 | $C_{21}H_{24}N_2O_7S$ | 56.24 | 5.39 | 6.25 | 56.09 | 5.43 | 6.24 |
| 31 | $C_{19}H_{16}N_2O_3Cl_2$ | 58.33 | 4.12 | 7.16 | 58.52 | 4.13 | 7.21 |
| 32 | $C_{20}H_{19}N_3O_5$ | 62.99 | 5.02 | 11.02 | 63.02 | 5.08 | 11.03 |
| 33 | $C_{44}H_{52}N_4O_7Cl_2$ | 64.46 | 6.39 | 6.83 | 64.09 | 6.22 | 6.96 |
| 34 | $C_{21}H_{23}N_2O_3Cl$ | 65.20 | 5.99 | 7.24 | 65.25 | 6.01 | 7.26 |
| 35 | $C_{21}H_{20}N_2O_3F_3Br$ | 51.97 | 4.15 | 5.77 | 52.22 | 4.14 | 5.89 |
| 36 | $C_{21}H_{23}N_2O_4Cl$ | 62.61 | 5.75 | 6.95 | 62.67 | 5.76 | 7.05 |
| 37 | $C_{21}H_{25}N_2O_7SP$ | 52.50 | 5.75 | 5.83 | 52.08 | 5.35 | 5.77 |
| 38 | $C_{20}H_{21}ClN_2O_4$ | 60.37 | 5.57 | 7.04 | 60.22 | 5.55 | 7.05 |
| 39 | $C_{21}H_{22}N_2O_4$ | 68.84 | 6.05 | 7.67 | 69.19 | 6.09 | 7.70 |
| 40 | $C_{20}H_{21}N_2O_3Cl$ | 64.43 | 5.68 | 7.51 | 64.71 | 5.76 | 7.54 |
| 41 | $C_{19}H_{18}N_2O_3$ | 70.79 | 5.63 | 8.69 | 70.96 | 5.66 | 8.62 |
| 42 | $C_{20}H_{21}N_2O_3Cl$ | 64.43 | 5.68 | 7.51 | 64.40 | 9.67 | 7.62 |
| 43 | $C_{21}H_{24}N_2O_4Cl_2$ | 57.41 | 5.50 | 6.38 | 57.02 | 5.79 | 6.25 |
| 44 | $C_{42}H_{53}N_4O_{18}S_2P_3$ | 47.98 | 5.04 | 5.29 | 48.06 | 5.08 | 5.43 |
| 45 | $C_{21}H_{22}N_2O_3$ | 71.98 | 6.33 | 7.99 | 72.32 | 6.35 | 8.02 |
| 46 | $C_{20}H_{17}F_3N_2O_2$ | 64.17 | 4.58 | 7.48 | 64.16 | 4.62 | 7.49 |
| 47 | $C_{20}H_{20}N_2O_2S$ | 68.16 | 5.72 | 7.95 | 68.19 | 5.76 | 8.14 |
| 48 | $C_{20}H_{21}ClN_2O_3S$ | 59.33 | 5.23 | 6.92 | 59.55 | 5.32 | 6.86 |
| 49 | $C_{20}H_{20}N_2O_2S_2$ | 62.47 | 5.24 | 7.29 | 62.16 | 5.16 | 7.12 |
| 50 | $C_{20}H_{21}N_2O_2SCl$ | 61.77 | 5.44 | 7.20 | 61.84 | 5.41 | 7.31 |
| 51 | $C_{20}H_{21}ClN_2O_3$ | 64.73 | 5.68 | 7.51 | 64.47 | 5.61 | 7.50 |
| 52 | $C_{21}H_{23}BrN_2O_2$ | 60.73 | 5.58 | 6.93 | 60.76 | 5.60 | 6.82 |
| 53 | $C_{19}H_{18}N_2O_3Cl_2$ | 58.03 | 4.61 | 7.12 | 57.97 | 4.65 | 7.11 |
| 54 | $C_{20}H_{17}N_3O_2$ | 72.49 | 5.17 | 12.68 | 72.16 | 5.26 | 12.54 |
| 55 | $C_{24}H_{20}N_2O_2$ | 78.24 | 5.47 | 7.60 | 78.22 | 5.47 | 7.50 |
| 56 | $C_{50}H_{44}Cl_2N_4O_9$ | 65.57 | 4.84 | 6.11 | 66.04 | 5.00 | 6.09 |
| 57 | $C_{25}H_{23}N_2O_2$ | 78.32 | 6.05 | 7.31 | 78.52 | 5.90 | 7.30 |
| 58 | $C_{20}H_{20}N_2O_2$ | 74.98 | 6.71 | 8.74 | 75.22 | 6.37 | 8.77 |
| 59 | $C_{18}H_{16}N_2O_2$ | 73.96 | 5.52 | 9.58 | 74.12 | 5.64 | 9.42 |
| 60 | $C_{18}H_{17}N_2O_2Cl$ | 65.75 | 5.21 | 8.52 | 65.85 | 5.29 | 8.56 |
| 61 | $C_{19}H_{19}ClN_2O_2$ | 66.56 | 5.59 | 8.17 | 66.80 | 5.61 | 8.12 |
| 62 | $C_{19}H_{19}N_2O_2Cl$ | 66.57 | 5.59 | 8.17 | 66.80 | 5.70 | 8.19 |
| 63 | $C_{19}H_{16}N_2O_2F_3Cl$ | 57.51 | 4.06 | 7.06 | 57.85 | 4.08 | 7.13 |
| 64 | $C_{19}H_{19}ClN_2O_3$ | 63.60 | 5.34 | 7.81 | 63.67 | 5.30 | 7.78 |
| 65 | $C_{19}H_{19}N_2O_2SCl$ | 60.87 | 5.11 | 7.47 | 60.97 | 5.30 | 7.39 |
| 66 | $C_{20}H_{21}N_2O_3Cl$ | 64.43 | 5.68 | 7.51 | 64.14 | 5.70 | 7.52 |
| 67 | $C_{18}H_{16}N_2O_2Cl_2$ | 59.52 | 4.44 | 7.71 | 59.26 | 4.42 | 7.67 |
| 68 | $C_{20}H_{20}N_2O_2Cl$ | 64.60 | 5.96 | 11.30 | 64.60 | 5.96 | 11.39 |
| 69 | $C_{21}H_{23}N_3O_2$ | 72.18 | 6.63 | 12.03 | 72.24 | 6.57 | 12.09 |
| 70 | $C_{19}H_{15}N_3O_2$ | 71.91 | 4.76 | 13.24 | 71.95 | 4.86 | 13.26 |
| 71 | $C_{19}H_{18}N_2O_4$ | 67.45 | 5.36 | 8.78 | 67.49 | 5.38 | 8.50 |
| 72 | $C_{18}H_{16}N_2O_3$ | 70.12 | 5.23 | 9.09 | 70.10 | 5.27 | 9.09 |
| 73 | $C_{18}H_{17}N_2O_3Cl$ | 62.70 | 4.97 | 8.12 | 62.53 | 4.93 | 8.18 |
| 74 | $C_{20}H_{21}ClN_2O_2$ | 67.32 | 5.93 | 7.85 | 67.22 | 5.92 | 7.83 |

TABLE 2-continued

Analytical Data on Examples 1-88

| Ex. | Empirical Formula | Calculated C | H | N | Found C | H | N |
|---|---|---|---|---|---|---|---|
| 75 | $C_{22}H_{24}N_2O_3$ | 72.51 | 6.64 | 7.69 | 72.56 | 6.55 | 7.67 |
| 76 | $C_{19}H_{17}N_2O_2Cl$ | 66.90 | 5.03 | 8.22 | 66.60 | 5.14 | 8.20 |
| 77 | $C_{20}H_{20}N_2O_3Cl_2$ | 58.98 | 4.95 | 6.88 | 58.90 | 4.94 | 6.90 |
| 78 | $C_{21}H_{24}N_2O_7S$ | 56.24 | 5.39 | 6.25 | 56.37 | 5.42 | 6.28 |
| 79 | $C_{19}H_{17}N_3O_5$ | 62.12 | 4.66 | 11.44 | 62.05 | 4.66 | 11.54 |
| 80 | $C_{23}H_{29}N_3O_{10}S$ | 51.20 | 5.42 | 7.79 | 51.20 | 5.36 | 8.01 |
| 81 | $C_{21}H_{25}ClN_2O_4$ | 62.30 | 6.22 | 6.92 | 62.49 | 6.23 | 6.94 |
| 82 | $C_{21}H_{23}ClN_2O_4$ | 62.61 | 5.75 | 6.95 | 62.72 | 5.76 | 7.04 |
| 83 | $C_{22}H_{25}N_3O_3$ | 69.64 | 6.64 | 11.07 | 69.73 | 6.64 | 11.07 |
| 84 | $C_{23}H_{27}N_3O_3$ | 70.21 | 6.92 | 10.68 | 70.42 | 6.95 | 10.67 |
| 85 | $C_{28}H_{31}N_3O_9$ | 60.75 | 5.64 | 7.59 | 60.89 | 5.69 | 7.53 |
| 86 | $C_{23}H_{31}Cl_2N_3O_4$ | 57.03 | 6.45 | 8.67 | 57.05 | 6.31 | 8.79 |
| 87 | $C_{22}H_{26}N_2O_6S$ | 59.18 | 5.87 | 6.27 | 59.16 | 5.93 | 6.25 |
| 88 | $C_{22}H_{26}N_2O_7S$ | 57.13 | 5.67 | 6.06 | 57.08 | 5.71 | 6.10 |

Pharmacology

The action of 4-amino-3-quinolinecarboxylic acids and esters of this invention on gastric secretion was studied in rats and dogs. Inhibition of secretion was measured and expressed in terms of percent of gastric acid output. Anti-ulcer studies were also done in rats. The results of studies with a preferred compound of this invention are described below. Other compounds of this invention show qualitatively similar effects in one or more of these tests.

TABLE 3

Effect of Compound of Example 1 on Stimulated Gastric Secretion

| Species | Dose (μmoles/kg) | Route | Stimulating Agent | Inhibition[1] (%) |
|---|---|---|---|---|
| Rat[2] | 0.3–8.1 | IV | Histamine | 43–96 |
| Rat[2] | 0.3–10.7 | ID | Histamine | 40–70 |
| Rat[2] | 0.3–8.1 | IV | Tetragastrin | 27–85 |
| Rat[2] | 0.9–8.1 | IV | Methacholine | 25–76 |
| Dog[3] | 2.7 and 8.1 | IV | Food | 50 and 83 |
| Dog[3] | 32.4 | PO | Food | 56 |

[1] Inhibition was measured as output of gastric acid.
[2] Rats were studied according to a modification of the method of Ghosh and Shield, 1958, Brit. J. Pharmacol. 13:54–61.
[3] Dogs were Heidenhain pouch dogs.

The compound of Example 1 was administered to pyloric-ligated rats having no artificial stimulation of gastric secretion. The doses used were 33 to 134 μmoles/kg; acid output was inhibited by 38–55%.

The gastric anti-ulcer effects of the compound of Example 1 were examined in rats studied according to the method of Shay et al., 1945, Gastroenterology 5:43–61. Protection against ulceration of 4–90% was provided by doses of 12–198 μmoles/kg.

Effective quantities of the foregoing compounds represented by Formula I may be administered to a living animal body for therapeutic purposes relating to the control of acid release due to histamine stimulation and peptic ulcer control or combatting peptic ulcers in mammals according to usual modes of administration for pharmaceuticals in usual forms such as orally in solution, emulsions, suspensions, pills, tablets, troches, lozenges, pellets, capsules and the like in pharmaceutically acceptable carriers; parenterally in the form of sterile solutions or mixtures.

The pharmaceutical carrier employed may be, for example, either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, arachis oil, water or any parenterally acceptable liquid.

Although very small quantities of the active materials of the present invention are effective when minor therapy for gastric irritation is involved or in cases of administration to subjects having a low body weight, unit dosages will usually contain the active ingredient in an amount to supply 2 to 6 mg/kg to the host. Unit dosages may vary from 100 to 500 mg active agent, preferably for an adult human from 200 to 500 mg. The active ingredient will preferably be administered in equal doses one to four times per day. The daily dosage regimen will vary from about 100 to about 1200 mg, most preferably from about 300 to 900 mg/day. It is only necessary that the active ingredient constitute an effective amount, i.e., such that a suitable effective dosage will be obtained consistent with the dosage form employed. The exact individual dosages as well as daily dosages will, of course, be determined according to standard medical principles under the direction of a physician or veterinarian.

The following formulations are representative:

| 1. | Capsules Ingredients | Amount, mg. |
|---|---|---|
| | Active ingredient, e.g., Example 1 = Ethyl 8-methoxy-4-(2-methylphenyl) amino-3-quinolinecarboxylate hydrochloride | 200 |
| | Sucrose | 100 |
| | Starch | 30 |
| | Talc | 5 |
| | Stearic Acid | 3 |
| | | 338 |

Blend and fill into gelatin capsules.

| 2. | Tablets Ingredients | Amount mg. per tablet |
|---|---|---|
| | Active ingredient e.g., Example 1 = Ethyl 8-methoxy-4-(2-methylphenyl) amino-3-quinolinecarboxylate hydrochloride | 350.0 |
| | Alginic acid | 20.0 |
| | Calcium and ammonium alginate | 40.0 |
| | Starch | 54.0 |
| | Lactose | 75.0 |
| | Magnesium stearate | 2.2 |
| | | 721.2 |

The mixture, all except the magnesium stearate and one half of the calcium ammonium alginate, is blended and granulated with ethanol and passed through a number eight mesh screen and the mixture dried 16 hours at 140° F. The dried granulated material is then blended thoroughly with the remainder of the calcium ammonium alginate and magnesium stearate and tableted.

| 3. | Intravenous Injection Ingredients | Amounts, mg. |
|---|---|---|
| | Active ingredient e.g., Example 1 = Ethyl 8-methoxy-4-(2-methylphenyl) amino-3-quinolinecarboxylate hydrochloride | 200 |
| | Water | 2,000 |
| | Preservative, e.g, chlorobutanol | 20 |
| | | 2,200 |

What is claimed is:

1. A method of inhibiting secretion of gastric acid and/or treating peptic ulcers in mammals which comprises administering to a mammal an effective amount of a compound having the formula:

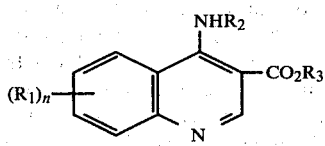

wherein;

$R_1$ is selected from the group consisting of loweralkyl, phenyl, O-loweralkyl, S-loweralkyl, halogen, trifluoromethyl, cyano and dialkylamino, $R_2$ is selected from the group consisting of loweralkyl, phenyl, phenylloweralkyl or phenyl substituted by 1-3 radicals taken from among loweralkyl, O-loweralkyl, S-loweralkyl, halogen, cyano, hydroxy, carbamoyl, carboxy, acetyl, trifluoromethyl and nitro, $R_3$ is selected from the group consisting of hydrogen, loweralkyl, loweralkyldimethylamino, loweralkyl-loweralkoxy, and allyl, n is 0, 1 or 2, and the pharmaceutically acceptable addition salts thereof.

2. The method of claim 1 wherein the compound is ethyl 8-methoxy-4-[(2-methylphenyl)amino]-3-quinolinecarboxylate.

3. The method of claim 1 wherein the compound is ethyl 8-methoxy-4-[(2-methylphenyl)amino]-3-quinolinecarboxylate hydrochloride.

4. The method of claim 1 wherein the compound is ethyl 8-methoxy-4-[(2-methoxyphenyl)amino]-3-quinolinecarboxylate.

5. The method of claim 1 wherein the compound is ethyl 8-methoxy-4-[(2-methoxyphenyl)amino]-3-quinolinecarboxylate hydrochloride.

6. The method of claim 1 wherein the compound is ethyl 8-methoxy-4-[(2-methylthiophenyl)amino]-3-quinolinecarboxylate.

7. The method of claim 1 wherein the compound is ethyl 8-methoxy-4-[(2-methylthiophenyl)amino]-3-quinolinecarboxylate hydrochloride.

8. The method of claim 1 wherein the compound is ethyl 8-methoxy-4-[(2-trifluoromethylphenyl)amino]-3-quinolinecarboxylate.

9. The method of claim 1 wherein the compound is ethyl 8-methoxy-4-[(2-trifluoromethylphenyl)amino]-3-quinolinecarboxylate hydrochloride.

10. The method of claim 1 wherein the compound is ethyl 4-[(2-ethoxyphenyl)amino]-8-methoxy-3-quinolinecarboxylate.

11. The method of claim 1 wherein the compound is ethyl 4-[(2-ethoxyphenyl)amino]-8-methoxy-3-quinolinecarboxylate hydrochloride.

12. The method of claim 1 wherein the compound is ethyl 4-[(2-ethylphenyl)amino]-8-methoxy-3-quinolinecarboxylate.

13. The method of claim 1 wherein the compound is ethyl 4-[(2-ethylphenyl)amino]-8-methoxy-3-quinolinecarboxylate phosphate (1:2).

14. The method of claim 1 wherein the compound is ethyl 4-[(2,6-dichlorophenyl)amino]-8-methoxy-3-quinolinecarboxylate.

15. The method of claim 1 wherein the compound is ethyl 8-ethoxy-4-[(2-methylphenyl)amino]-3-quinolinecarboxylate.

16. The method of claim 1 wherein the compound is ethyl 8-ethoxy-4-[(2-methylphenyl)amino]-3-quinolinecarboxylate hydrochloride.

17. The method of claim 1 wherein the compound is ethyl 8-ethoxy-4-[(2-methoxyphenyl)amino]-3-quinolinecarboxylate.

18. The method of claim 1 wherein the compound is ethyl 8-ethoxy-4-[(2-methoxyphenyl)amino]-3-quinolinecarboxylate hydrochloride.

19. The method of claim 1 wherein the compound is ethyl 8-methoxy-4-[(2-methoxyphenyl)amino]-5-methyl-3-quinolinecarboxylate.

20. The method of claim 1 wherein the compound is ethyl 8-methoxy-4-[(2-methoxyphenyl)amino]-5-methyl-3-quinolinecarboxylate dihydrochloride.

21. The method of claim 1 wherein the compound is ethyl 4-[(2-methoxyphenyl)amino]-8-methyl-3-quinolinecarboxylate.

22. The method of claim 1 wherein the compound is ethyl 4-[(2-methoxyphenyl)amino]-8-methyl-3-quinolinecarboxylate hydrochloride.

23. The method of claim 1 wherein the compound is ethyl 4-[(2-methoxyphenyl)amino]-3-quinolinecarboxylate.

24. The method of claim 1 wherein the compound is ethyl 4-[(2-methoxyphenyl)amino]-3-quinolinecarboxylate hydrochloride.

25. The method of claim 1 wherein the compound is ethyl 4-{[2-(methylthio)phenyl]amino}-3-quinolinecarboxylate.

26. The method of claim 1 wherein the compound is ethyl 4-{[2-(methylthio)phenyl]amino}-3-quinolinecarboxylate hydrochloride.

27. The method of claim 1 wherein the compound is ethyl 8-methyl-4-[(2-methylphenyl)amino]-3-quinolinecarboxylate, monohydrochloride.

28. The method of claim 1 wherein the compound is ethyl 8-methoxy-4-{[2-(1-methylethyl)phenyl]amino}-3-quinolinecarboxylate.

29. The method of claim 1 wherein the compound is ethyl 8-chloro-4-[(2-methylphenyl)amino]-3-quinolinecarboxylate.

30. The method of claim 1 wherein the compound is ethyl 4-[(2-chloro-6-methylphenyl)amino]-8-methoxy-3-quinolinecarboxylate, monohydrochloride.

31. The method of claim 1 wherein the compound is ethyl 8-methoxy-4-[(2,3-dimethylphenyl)amino]-3-quinolinecarboxylate, monosulfate.

32. The method of claim 1 wherein the compound is 1-methylethyl 8-methoxy-4-[(2-methylphenyl)amino]-3-quinolinecarboxylate, monohydrochloride, monohydrate.

33. The method of claim 1 wherein the compound is ethyl 8-methoxy-4-[(2-methylphenyl)amino]-3-quinolinecarboxylate, ethanesulfonate (1:1)(salt).

34. The method of claim 1 wherein the compound is ethyl 8-methoxy-4-[(2-methylphenyl)amino]-3-quinolinecarboxylate, 2-hydroxyethanesulfonate (1:1)(salt).

35. The method of claim 1 wherein the compound is ethyl 8-methoxy-4-[(2,6-dimethylphenyl)amino]-3-quinolinecarboxylate.

36. The method of claim 1 wherein the compound is ethyl 8-methoxy-4-[(2,6-dimethylphenyl)amino]-3-quinolinecarboxylate hydrobromide.

37. The method of claim 1 wherein the compound is ethyl 4-[(2-methylphenyl)amino]-3-quinolinecarboxylate hydrochloride.

38. The method of claim 1 wherein the compound is ethyl 8-dimethylamino-4-[(2-methylphenyl)amino]-3-quinolinecarboxylate.

39. A compound particularly effective in control of gastric secretion and/or treatment or prevention of peptic ulcers selected from 4-amino-3-quinolinecarboxylate having the formula:

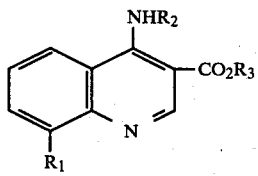

wherein;
R₁ is selected from the group consisting of loweralkyl, phenyl, O-loweralkyl, S-loweralkyl, halogen, trifluoromethyl, cyano and dialkylamino,
R₂ is selected from the group consisting of loweralkyl, phenyl, phenylloweralkyl or phenyl substituted by 1-3 radicals taken from among loweralkyl, O-loweralkyl, S-loweralkyl, halogen, cyano, hydroxy, carbamoyl, carboxy, acetyl, trifluoromethyl and nitro,
R₃ is selected from the group consisting of hydrogen, loweralkyl, loweralkyldimethylamino, loweralkylloweralkoxy, and allyl, and
the pharmaceutically acceptable addition salts thereof.

40. The compound of claim 39 which is ethyl 8-methoxy-4-[(2-methylphenyl)amino]-3-quinolinecarboxylate.

41. The compound of claim 39 which is ethyl 8-methoxy-4-[(2-methylphenyl)amino]-3-quinolinecarboxylate hydrochloride.

42. The compound of claim 39 which is ethyl 8-methoxy-4-[(2-methoxyphenyl)amino]-3-quinolinecarboxylate.

43. The compound of claim 39 which is ethyl 8-methoxy-4-[2-methoxyphenyl)amino]-3-quinolinecarboxylate hydrochloride.

44. The compound of claim 39 which is ethyl 8-methoxy-4-[(2-methylthiophenyl)amino]-3-quinolinecarboxylate.

45. The compound of claim 39 which is ethyl 8-methoxy-4-[(2-methylthiophenyl)amino]-3-quinolinecarboxylate hydrochloride.

46. The compound of claim 39 which is ethyl 8-methoxy-4-[(2-trifluoromethylphenyl)amino]-3-quinolinecarboxylate.

47. The compound of claim 39 which is ethyl 8-methoxy-4-[(2-trifluoromethylphenyl)amino]-3-quinolinecarboxylate hydrochloride.

48. The compound of claim 39 which is ethyl 4-[(2-ethoxyphenyl)amino]-8-methoxy-3-quinolinecarboxylate.

49. The compound of claim 39 which is ethyl 4-[(2-ethoxyphenyl)amino]-8-methoxy-3-quinolinecarboxylate hydrochloride.

50. The compound of claim 39 which is ethyl 4-[(2-ethylphenyl)amino]-8-methoxy-3-quinolinecarboxylate.

51. The compound of claim 39 which is ethyl 4-[(2-ethylphenyl)amino]-8-methoxy-3-quinolinecarboxylate phosphate (1:2).

52. The compound of claim 39 which is ethyl 4-[(2,6-dichlorophenyl)amino]-8-methoxy-3-quinolinecarboxylate.

53. The compound of claim 39 which is ethyl 8-ethoxy-4-[(2-methylphenyl)amino]-3-quinolinecarboxylate.

54. The compound of claim 39 which is ethyl 8-ethoxy-4-[(2-methylphenyl)amino]-3-quinolinecarboxylate hydrochloride.

55. The compound of claim 39 which is ethyl 8-ethoxy-4-[(2-methoxyphenyl)amino]-3-quinolinecarboxylate.

56. The compound of claim 39 which is ethyl 8-ethoxy-4-[(2-methoxyphenyl)amino]-3-quinolinecarboxylate hydrochloride.

57. The compound of claim 39 which is ethyl 8-methoxy-4-[(2-methoxyphenyl)amino]-5-methyl-3-quinolinecarboxylate.

58. The compound of claim 39 which is ethyl 8-methoxy-4-[(2-methoxyphenyl)amino]-5-methyl-3-quinolinecarboxylate dihydrochloride.

59. The compound of claim 39 which is ethyl 4-[(2-methoxyphenyl)amino]-8-methyl-3-quinolinecarboxylate.

60. The compound of claim 39 which is ethyl 4-[(2-methoxyphenyl)amino]-8-methyl-3-quinolinecarboxylate hydrochloride.

61. The compound of claim 39 which is ethyl 8-methyl-4-[(2-methylphenyl)amino]-3-quinolinecarboxylate, monohydrochloride.

62. The compound of claim 39 which is ethyl 8-methoxy-4-[[2-(1-methylethyl)phenyl]amino]-3-quinolinecarboxylate.

63. The compound of claim 39 which is ethyl 8-chloro-4-[(2-methylphenyl)amino]-3-quinolinecarboxylate.

64. The compound of claim 39 which is ethyl 4-[(2-chloro-6-methylphenyl)amino]-8-methoxy-3-quinolinecarboxylate, monohydrochloride.

65. The compound of claim 39 which is ethyl 8-methoxy-4-[(2,3-dimethylphenyl)amino]-3-quinolinecarboxylate, monosulfate.

66. The compound of claim 39 which is 1-methylethyl 8-methoxy-4-[2-methylphenyl)amino]-3-quinolinecarboxylate, monohydrochloride, monohydrate.

67. The compound of claim 39 which is ethyl 8-methoxy-4-[(2-methylphenyl)amino]-3-quinolinecarboxylate, ethanesulfonate (1:1)(salt).

68. The compound of claim 39 which is ethyl 8-methoxy-4-[(2-methylphenyl)amino]-3-quinolinecarboxylate, 2-hydroxyethanesulfonate (1:)(salt).

69. The compound of claim 39 which is ethyl 8-methoxy-4-[(2,6-dimethylphenyl)amino]-3-quinolinecarboxylate.

70. The compound of claim 39 which is ethyl 8-methoxy-4-[(2,6-dimethylphenyl)amino]-3-quinolinecarboxylate hydrobromide.

71. The compound of claim 39 which is ethyl 8-dimethylamino-4-[(2-methylphenyl)amino]-3-quinolinecarboxylate.

72. A pharmaceutical composition for inhibiting secretion of gastric acid and/or treating peptic ulcer in mammals comprised of a pharmaceutical carrier and an effective amount of a compound having the formula:

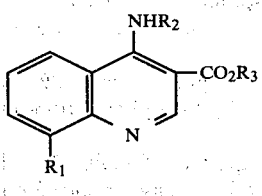

wherein;
$R_1$ is selected from the group consisting of loweralkyl, phenyl, O-loweralkyl, S-loweralkyl, halogen, trifluoromethyl cyano and dialkylamino,
$R_2$ is selected from the group consisting of loweralkyl, phenyl, phenylloweralkyl or phenyl substituted by 1–3 radicals taken from among loweralkyl, O-loweralkyl, S-loweralkyl, halogen, cyano, hydroxy, carbamoyl, carboxy, acetyl, trifluoromethyl and nitro,
$R_3$ is selected from the group consisting of hydrogen, loweralkyl, loweralkyldimethylamino, loweralkyl-loweralkoxy, and allyl, and
the pharmaceutically acceptable addition salts thereof.

73. The composition of claim 72 wherein the compound is ethyl 8-methoxy-4-[(2-methylphenyl)amino]-3-quinolinecarboxylate.

74. The composition of claim 72 wherein the compound is ethyl 8-methoxy-4-[(2-methylphenyl)amino]-3-quinolinecarboxylate hydrochloride.

75. The composition of claim 72 wherein the compound is ethyl 8-methoxy-4-[(2-methoxyphenyl)amino]-3-quinolinecarboxylate.

76. The composition of claim 72 wherein the compound is ethyl 8-methoxy-4-[(2-methoxyphenyl)amino]-3-quinolinecarboxylate hydrochloride.

77. The composition of claim 72 wherein the compound is ethyl 8-methoxy-4-[(2-methylthiophenyl)amino]-3-quinolinecarboxylate.

78. The composition of claim 72 wherein the compound is ethyl 8-methoxy-4-[(2-methylthiophenyl)amino]-3-quinolinecarboxylate hydrochloride.

79. The composition of claim 72 wherein the compound is ethyl 8-methoxy-4-[(2-trifluoromethylphenyl)amino]-3-quinolinecarboxylate.

80. The composition of claim 72 wherein the compound is ethyl 8-methoxy-4-[(2-trifluoromethylphenyl)amino]-3-quinolinecarboxylate hydrochloride.

81. The composition of claim 72 wherein the compound is ethyl 4-[(2-ethoxyphenyl)amino]-8-methoxy-3-quinolinecarboxylate.

82. The composition of claim 72 wherein the compound is ethyl 4-[(2-ethoxyphenyl)amino]-8-methoxy-3-quinolinecarboxylate hydrochloride.

83. The composition of claim 72 wherein the compound is ethyl 4-[(2-ethylphenyl)amino]-8-methoxy-3-quinolinecarboxylate.

84. The composition of claim 72 wherein the compound is ethyl 4-[(2-ethylphenyl)amino]-8-methoxy-3-quinolinecarboxylate phosphate (1:2).

85. The composition of claim 72 wherein the compound is ethyl 4-[(2,6-dichlorophenyl)amino]-8-methoxy-3-quinolinecarboxylate.

86. The composition of claim 72 wherein the compound is ethyl 8-ethoxy-4-[(2-methylphenyl)amino]-3-quinolinecarboxylate.

87. The composition of claim 72 wherein the compound is ethyl 8-ethoxy-4-[(2-methylphenyl)amino]-3-quinolinecarboxylate hydrochloride.

88. The composition of claim 72 wherein the compound is ethyl 8-ethoxy-4-[(2-methoxyphenyl)amino]-3-quinolinecarboxylate.

89. The composition of claim 72 wherein the compound is ethyl 8-ethoxy-4-[(2-methoxyphenyl)amino]-3-quinolinecarboxylate hydrochloride.

90. The composition of claim 72 wherein the compound is ethyl 8-methoxy-4-[(2-methoxyphenyl)amino]-5-methyl-3-quinolinecarboxylate.

91. The composition of claim 72 wherein the compound is ethyl 8-methoxy-4-[(2-methoxyphenyl)amino]-5-methyl-3-quinolinecarboxylate dihydrochloride.

92. The composition of claim 72 wherein the compound is ethyl 4-[(2-methoxyphenyl)amino]-8-methyl-3-quinolinecarboxylate.

93. The composition of claim 72 wherein the compound is ethyl 4-[(2-methoxyphenyl)amino]-8-methyl-3-quinolinecarboxylate hydrochloride.

94. The composition of claim 72 wherein the compound is ethyl 8-methoxy-4-[(2,6-dimethylphenyl)amino]-3-quinolinecarboxylate.

95. The composition of claim 72 wherein the compound is ethyl 8-methoxy-4-[(2,6-dimethylphenyl)amino]-3-quinolinecarboxylate hydrobromide.

96. The composition of claim 72 wherein the compound is ethyl 8-methyl-4-[(2-methylphenyl)amino]-3-quinolinecarboxylate, monohydrochloride.

97. The composition of claim 72 wherein the compound is ethyl 8-methoxy-4-[[2-(1-methylethyl)phenyl]amino]-3-quinolinecarboxylate.

98. The composition of claim 72 wherein the compound is ethyl 8-chloro-4-[(2-methylphenyl)amino]-3-quinolinecarboxylate.

99. The composition of claim 72 wherein the compound is ethyl 4-[(2-chloro-6-methylphenyl)amino]-8-methoxy-3-quinolinecarboxylate, monohydrochloride.

100. The composition of claim 72 wherein the compound is ethyl 8-methoxy-4-[(2,3-dimethylphenyl)amino]-3-quinolinecarboxylate, monosulfate.

101. The composition of claim 72 wherein the compound is 1-methylethyl 8-methoxy-4-[(2-methylphenyl)amino]-3-quinolinecarboxylate, monohydrochloride, monohydrate.

102. The composition of claim 72 wherein the compound is ethyl 8-methoxy-4-[(2-methylphenyl)amino]-3-quinolinecarboxylate, ethanesulfonate (1:1)(salt).

103. The composition of claim 72 wherein the compound is ethyl 8-methoxy-4-[(2-methylphenyl)amino]-3-quinolinecarboxylate, 2-hydroxyethanesulfonate (1:1)(salt).

104. The composition of claim 72 wherein the compound is ethyl 8-dimethylamino-4-[(2-methylphenyl)amino]-3-quinolinecarboxylate.

* * * * *